United States Patent
Arshintseva et al.

(10) Patent No.: US 12,310,982 B2
(45) Date of Patent: May 27, 2025

(54) USE OF THE POLOXAMER AS A PHARMACOLOGICALLY ACTIVE SUBSTANCE

(71) Applicants: Elena Valentinovna Arshintseva, Saransk (RU); Sergei Yurevich Pushkin, Noginsk (RU)

(72) Inventors: Elena Valentinovna Arshintseva, Saransk (RU); Sergei Yurevich Pushkin, Noginsk (RU)

( * ) Notice: Subject to any disclaimer, the term of this patent is extended or adjusted under 35 U.S.C. 154(b) by 769 days.

(21) Appl. No.: 17/055,139

(22) PCT Filed: Dec. 10, 2018

(86) PCT No.: PCT/RU2018/000804
§ 371 (c)(1),
(2) Date: Nov. 13, 2020

(87) PCT Pub. No.: WO2020/122745
PCT Pub. Date: Jun. 18, 2020

(65) Prior Publication Data
US 2021/0085710 A1  Mar. 25, 2021

(51) Int. Cl.
*A61K 31/765* (2006.01)
*A61P 7/06* (2006.01)

(52) U.S. Cl.
CPC ............. *A61K 31/765* (2013.01); *A61P 7/06* (2018.01)

(58) Field of Classification Search
None
See application file for complete search history.

(56) References Cited

U.S. PATENT DOCUMENTS

| 2015/0093368 A1 | 4/2015 | Emanuele |
| 2016/0000823 A1* | 1/2016 | Emanuele ............ A61K 38/482 424/78.38 |
| 2022/0023333 A1* | 1/2022 | Arshintseva ............ A61K 9/08 |

FOREIGN PATENT DOCUMENTS

| RU | 2642302 C1 | 1/2018 |
| WO | 2010144904 A1 | 12/2010 |
| WO | 2017007917 A1 | 1/2017 |

OTHER PUBLICATIONS

Litvinov et al., Role of red blood cells in haemostasis and thrombosis. ISBT Sci Ser. 2017; 12(1):176-183 (Year: 2017).*
Sandor B. et.al. Effects of Poloxamer 188 on red blood cell membrance properties in sickle cell anaemia. Br J Haematol. Apr. 2016; 173(1):145-9, doi:10.1111/bjh.13937. Epub Feb. 5, 2016. abstract.

* cited by examiner

*Primary Examiner* — Aradhana Sasan

(57) ABSTRACT

The invention relates to the field of medicine and veterinary medicine, in particular to a new use of the poloxamer as a pharmacologically active substance A new use of the poloxamer as a pharmacologically active substance to increase the levels of haemoglobin and red blood cells in a patients blood is revealed. Thus, new pharmacologically active substances that promote a rise in haemoglobin and red blood cell levels in a patients blood were found, the use of which ensures the achievement of the technical result consisting in a significant reduction of the toxic effect and side effects of these substances on the patients body in the case of oral and parenteral administration.

10 Claims, No Drawings

USE OF THE POLOXAMER AS A PHARMACOLOGICALLY ACTIVE SUBSTANCE

The invention relates to the field of medicine and veterinary medicine, in particular to a new use of the poloxamer as a pharmacologically active substance to increase the levels of haemoglobin and red blood cells in the blood.

Intensive production of red blood cells and their simultaneous decomposition continuously occur in the body. By anaemia is meant a condition characterized by an imbalance of red blood cells, i.e. by a decrease in production rate or increased destruction of red blood cells, or a combination of both factors. In most cases, quantitative measures of haemoglobin and/or red blood cells are quite sufficient for recognition of anaemia. Since the main function of red blood cells and haemoglobin contained in them is to transport oxygen to the tissues, a decrease in the red blood cell and haemoglobin count causes the development of tissue hypoxia. Thus, anaemia is a condition that is characterized by a decrease in the haemoglobin content (up to 115-110 g/l and below) and/or red blood cell count (up to $3.8-3.6*10^{12}$/l and below) per unit of blood volume, leading to a failure in tissue oxygen supply (Папаян А. В., Жукова Жукова. Анемии у детей : руководство для врачей .—СПб : Питер, 2001.—384 с. (Papayan A. V., Zhukova L. Yu. Anemii u detey: rukovodstvo dlya vrachey.—St. P.: Piter, 2001.—384 p.))

In the case of anaemia the gas exchange in the body is disturbed, chronic fatigue, increased sleepiness, dizziness, exhaustion occur, irritability is increased. In severe cases anaemia can lead to the shock states, pronounced hypotension, coronary, pulmonary insufficiency, haemorrhagic shock, as well as disorders of cellular metabolism. Early diagnosis and treatment of anaemia facilitate an elimination of the above-mentioned conditions. The World Health Organization data suggest that anaemia needs to be paid close attention, since the issues of diagnosis and the capabilities of modern therapy are still understudied.

The use of various forms of the recombinant erythropoietin to increase the red blood cell count in a variety of clinical situations, in particular for treatment of anaemia, is known. Erythropoietin is a growth factor that is essential at the final stages of the erythroid lineage differentiation. It is intended to maintain packed red blood cells in accordance with the body's need for oxygen (ЖибуртЕ. Б Трансфузиология : учебник /Е. Б . Жибурт .—СПб : Питер, 2002.—736 с. (Zhiburt E. B. Transfuziologiya: uchebnik/E. B. Zhiburt. St. P.: Piter, 2002.—736 p.)). For example, US patent application 2015093368, published on 2 Apr. 2015, discloses both the use of erythropoietin for stimulation of red blood cell production and the use of poloxamers for maintaining the flexibility of red blood cells and increasing microcirculatory, blood flow, thereby improving tissue oxygenation.

Treatment with erythropoietin for several weeks usually leads to an increase in haemoglobin content of approximately 10-30 g/l in healthy people. In most cases, when erythropoietin is administered to patients with anaemia, there observed a significant increase in the haemoglobin level and red blood cell count, which contributes to both improving a quality of life and increasing longevity in a patient.

However, the use of erythropoietin may be accompanied by a number of side effects described in the document RU2642302 published on 24.01.18. Recently disclosed information suggests that the use of higher doses of erythropoietin may be associated with an increased risk of cardiovascular diseases, tumor growth and mortality in some patient populations (Kraft et al., 2009, Clin J Am Soc Nephrol 4:470-480; Glaspy, 2009, Annu Rev Med 60:181-192). Also, erythropoietin does not always show efficacy, and many patients are resistant to high doses of the said active substance (Horl et al. (2000) Nephrol Dial Transplant 15, 43-50). In addition, more than 50% of patients suffering from malignant diseases have an inadequate response to erythropoietin. About 10% of patients with severe kidney disease have a decreased response to erythropoietin (Glaspy et al. (1997) J Clin Oncol 15, 1218-1234; Demetri et al. (1998) J Clin Oncol 16, 3412-3425). Only less than 10% of patients with myelodysplastic syndrome are known to respond favourably to treatment with erythropoietin (Estey (2003) Curr Opin Hematol 10, 60-67). In turn, a poor response to treatment with erythropoietin is predicted in the case of the following conditions: inflammatory processes, hyperparathyroidism, deficiency of iron and vitamins, as well as due to inadequate dialysis and toxic effect of aluminium. The molecular mechanisms of erythropoietin resistance are still unclear.

Thus, disadvantages of erythropoietin usage may include insufficient effectiveness in a number of the above cases, as well as the appearance of adverse effects caused by higher doses of erythropoietin. It should also be noted that the cultivation of erythropoietin is quite a time-consuming and a complex process.

The task underlying the present invention is to identify new pharmacologically active substances that promote a rise in haemoglobin and red blood cell levels in a patient's blood, the use of which will ensure the achievement of the technical result consisting in a significant reduction of the toxic effect and side effects of these substances on the patient's body in the case of oral and parenteral administration.

The task set is solved through the use of the poloxamer as a pharmacologically active substance to increase the levels of haemoglobin and red blood cells in a patient's blood.

Poloxamers are polyoxyethylene and polyoxypropylene block copolymers, which are used not only as auxiliary substances, but also as medicinal agents having useful biological properties.

Poloxamer has the most widespread use as an emulsifier for fatty emulsions for intravenous administration, as well as a stabilizer that provides transparency to elixirs and syrups. In addition, poloxamer is used as a wetting agent in eye drops, ointments, gels and as a binding agent in tablets. Poloxamers are also used in the treatment of pathological hydrophobic interactions in the blood and in other biological fluids, as they improve blood flow and reduce the adhesion of macromolecules and cells.

Commercial poloxamers are known under the following trade names: Proxanol, Emuxol, Kolliphor, Pluronic, Synperonic, Lutrol.

In view of specific properties of poloxamers that define their use in medicine and veterinary medicine, the inventors suggested a use of the poloxamer for increasing the levels of haemoglobin and red blood cells in a patient's blood, excluding the use of the recombinant erythropoietin, thereby preventing adverse events caused by the use of the aforementioned hormone. There were found poloxamer properties to stimulate the erythrocyte lineage of the bone marrow, thus ensuring the achievement of the said purposes. In addition, it is known that poloxamers are low toxic substances and do not have side effects intrinsic to erythropoietin when administered to a patient.

The term "patient", as used herein, refers to mammals, including, but not limited to, rats and human.

The use of the poloxamer is desirable for a patient whose initial levels of haemoglobin and red blood cells in the blood are below normal or normal.

The term "initial levels of haemoglobin and red blood cells", as used herein, refers to a quantitative measure of haemoglobin and red blood cells in a patient's blood prior to therapy.

Although it is possible to administer the active ingredient separately, it may be preferable to use it in the form of pharmaceutical formulations. Such formulations according to the present invention both for veterinary use and for use in humans, comprise at least one active ingredient, as defined above, together with one or more pharmacologically acceptable carriers therefor and optionally other therapeutic ingredients. The carrier(s) must be "acceptable" in the sense of being compatible with the other ingredients of the formulation and physiologically innocuous to the recipient.

In a preferred embodiment of the present invention, a pharmaceutical composition comprising poloxamer as a pharmacologically active substance and at least one auxiliary substance is used to increase the levels of haemoglobin and red blood cells in a patient's blood.

Preferably, a pharmaceutical composition with the poloxamer concentration of 0.1-80 wt % is used.

In yet another preferred embodiment of the present invention, a pharmaceutical composition presented in the form of a tablet, effervescent tablet, capsule, powder, solution or emulsion is used.

The said compositions contemplate oral and parenteral administration.

One of the acceptable solid forms of the pharmaceutical composition of the present invention are tablets containing the active ingredient in a mixture with non-toxic pharmacologically acceptable excipients that are suitable for the tablet manufacturing. These excipients may be, for example, inert diluents, such as calcium or sodium carbonate, lactose, lactose monohydrate, croscarmellose sodium, povidone, calcium or sodium phosphate; granulating and disintegrating agents such as corn starch or alginic acid; binders such as cellulose, microcrystalline cellulose, starch, gelatin, or acacia; and lubricants such as magnesium stearate, stearic acid or talc.

Other acceptable solid form of the pharmaceutical composition of the present invention, suitable for oral administration, are hard gelatin capsules wherein the active ingredient is mixed with an inert solid diluent, or soft gelatin capsules wherein the active ingredient is mixed with an aqueous or oil medium.

Solution formulations according to the present invention, suitable for oral and patenteral administration, may be presented in the form of aqueous solutions or emulsions of perfluoroorganic compounds, wherein water for injection or purified water are preferred solvents.

Parenterally administered pharmaceutical compositions according to the present invention may be presented in the form of a sterile composition for injection, such as a sterile aqueous solution. Further, the aqueous formulations may include metal salts such as sodium chloride, potassium chloride, magnesium chloride, as well as the following additional components: glucose, ascorbic acid, inosine. In this case the quantitative content of additional components in the said composition is as follows: for sodium chloride—0.3-0.9 wt %, for potassium chloride—0.03-0.04 wt %, for magnesium chloride—0.01-0.02 wt %, for glucose—0.5-10 wt %, for ascorbic acid—0.1-1.0 wt %, and for inosine—0.1-1.0 wt %.

Formulations of compositions for oral and parenteral administration in the form of emulsions of perfluoroorganic compounds with the concentration of the poloxamer in the range of 1-16 wt %/l comprise perfluorodecalin and perfluoromethylcyclohexylpiperidine in concentrations of 0.001-60 wt %/l, emulsifying and stabilizing additive, and may further comprise sodium chloride, potassium chloride, magnesium chloride, sodium hydrogen carbonate, sodium phosphate monobasic and glucose.

Solutions and emulsions comprising poloxamer can be packaged in containers, such as ampoules or vials.

Formulations of pharmaceutical compositions according to the present invention can be prepared by any method known in the pharmaceutical art.

For example, tablets, capsules, powders are manufactured according to known techniques for solid dosage form production, for example, by wet granulation method, followed by addition of a lubricant to the dry granules, molding the final mixture of ingredients to form a dosage form of a given configuration and size, and by coating, if necessary.

Solutions for oral and parenteral administration are prepared through the use of an appropriate solvent, and in the case of solutions for injection, following all aseptic rules.

In turn, to obtain, for example, emulsions of perfluoroorganic compounds, a common method is used, which is based on the techniques that utilize ultrasound or homogenization on disintegrators under high pressure.

The use of the composition of the present invention is desirable for a patient whose initial levels of haemoglobin and red blood cells in the blood are below normal or normal.

Below are given examples of the use of the poloxamer and a pharmaceutical composition comprising poloxamer to increase the initial levels of haemoglobin and red blood cells in human and rat blood, using such poloxamer-188 trademarks as Lutrol F68 (BASF) and Emuxol-268 of Grade "A".

EXAMPLE 1. INTRAVENOUS ADMINISTRATION OF THE PHARMACEUTICAL COMPOSITION COMPRISING 0.1 WT % POLOXAMER TO RATS

Male and female outbred white rats were used in this experiment (the number of rats in the group was 6 individuals of each sex). The initial level of haemoglobin was 132.53 g/l, the initial level of red blood cells was $6.05 \times 10^{12}$/l. 400 mg/kg of an aqueous solution comprising 0.1 wt % poloxamer-188 (Lutrol F68), 0.9 wt % sodium chloride and water for injection as the remaining part was administered for 14 days. Following the use of the above pharmaceutical composition the level of haemoglobin was 138.49 g/l, the level of red blood cells was $6.30 \times 10^{12}$/l.

EXAMPLE 2. INTRAVENOUS ADMINISTRATION OF THE PHARMACEUTICAL COMPOSITION COMPRISING 4.0 WT % POLOXAMER TO RATS

Male and female outbred white rats were used in this experiment (the number of rats in the group was 6 individuals of each sex). The initial level of haemoglobin was 133.66 g/l, the initial level of red blood cells was $5.90 \times 10^{12}$/l. 400 mg/kg of an aqueous solution comprising 4.0 wt % poloxamer-188 (Emuxol-268 of Grade "A"), 0.9 wt % sodium chloride and water for injection as the remaining part was administered for 14 days. Following the use of the above pharmaceutical composition the level of haemoglobin was 140.08 g/l, the level of red blood cells was $6.61\times10^{12}$/l.

EXAMPLE 3. INTRAVENOUS ADMINISTRATION OF THE PHARMACEUTICAL COMPOSITION COMPRISING 16.0 WT % POLOXAMER TO RATS

Male and female outbred white rats were used in this experiment (the number of rats in the group was 6 individuals of each sex). The initial level of haemoglobin was 131.95 g/l, the initial level of red blood cells was $5.49\times10^{12}$/l. 400 mg/kg of an aqueous solution comprising 16.0 wt % poloxamer-188 (Emuxol-268 of Grade "A"), 0.9 wt % sodium chloride and water for injection as the remaining part was administered for 14 days. Following the use of the above pharmaceutical composition the level of haemoglobin was 136.88 g/l, the level of red blood cells was $5.60\times10^{12}$/l.

EXAMPLE 4. ORAL ADMINISTRATION OF THE PHARMACEUTICAL COMPOSITION COMPRISING 4.0 WT % POLOXAMER TO RATS

Male outbred white rats were used in this experiment (6 individuals). The initial level of haemoglobin was 163.57 g/l, the initial level of red blood cells was $8.99\times10^{12}$/l. 48 mg/kg of an aqueous solution comprising 4.0 wt % poloxamer-188 (Emuxol-268 of Grade "A") and water for injection as the remaining part was administered for 14 days. Following the use of the above pharmaceutical composition the level of haemoglobin was 170.00 g/l, the level of red blood cells was $9.62\times10^{12}$/l.

EXAMPLE 5. ORAL ADMINISTRATION OF THE PHARMACEUTICAL COMPOSITION COMPRISING 13.3 WT % POLOXAMER TO RATS

Male outbred white rats were used in this experiment (6 individuals). The initial level of haemoglobin was 157.00 g/l, the initial level of red blood cells was $8.41\times10^{12}$/l. 48 mg/kg of an aqueous solution comprising 13.3 wt % poloxamer-188 (Emuxol-268 of Grade "A") and water for injection as the remaining part was administered for 14 days. Following the use of the above pharmaceutical composition the level of haemoglobin was 162.00 g/l, the level of red blood cells was $8.80\times10^{12}$/l.

EXAMPLE 6. ORAL ADMINISTRATION OF THE PHARMACEUTICAL COMPOSITION COMPRISING 16 WT % POLOXAMER TO RATS

Male outbred white rats were used in this experiment (6 individuals). The initial level of haemoglobin was 163.00 g/l, the initial level of red blood cells was $8.98\times10^{12}$/l. 48 mg/kg of an aqueous solution comprising 16 wt % poloxamer-188 (Emuxol-268 of Grade "A"), 0.6 wt % sodium chloride and water for injection as the remaining part was administered for 14 days. Following the use of the above pharmaceutical composition the level of haemoglobin was 170.00 g/l, the level of red blood cells was $9.62\times10^{12}$/l.

EXAMPLE 7. ORAL ADMINISTRATION OF THE PHARMACEUTICAL COMPOSITION COMPRISING 16.0 WT % POLOXAMER TO RATS

Male outbred white rats were used in this experiment (6 individuals). The initial level of haemoglobin was 162.00 g/l, the initial level of red blood cells was $8.83\times10^{12}$/l. 48 mg/kg of an aqueous solution comprising 16.0 wt % poloxamer-188 (Emuxol-268 of Grade "A") and water for injection as the remaining part was administered for 14 days. Following the use of the above pharmaceutical composition the level of haemoglobin was 173.00 g/l, the level of red blood cells was $9.57\times10^{12}$/l.

Also in these experiments the morphology of cells in peripheral blood smears of male and female rats was studied, and the appearance of singular oxyphilic normoblasts and an increase in the total reticulocyte count were observed, indicating the stimulation of erythropoiesis (stimulation of erythrocyte lineage in the bone marrow).

The study conducted revealed that levels of haemoglobin and red blood cells in the rat blood after parenteral and oral administration of the poloxamer or pharmaceutical compositions thereof increased, furthermore, the inventors did not find any side effects. Oral administration of a 10-fold therapeutic dose of the poloxamer—480 mg/kg to rats confirmed the absence of intoxication in animals.

EXAMPLE 8. INTRAVENOUS ADMINISTRATION OF THE PHARMACEUTICAL COMPOSITION COMPRISING 4.0 WT % POLOXAMER TO A HEALTHY PERSON

Volunteer patient B., man, 54 years of age. Diagnosis: healthy. The initial level of haemoglobin was 150 g/l, the initial level of red blood cells was $4.91\times10^{12}$/l. Sterile pyrogen-free aqueous solution of the poloxamer comprising 4.0 wt % poloxamer-188 (Emuxol-268 of Grade "A"), 0.9 wt % sodium chloride and water for injection as the remaining part. 10 ml was intravenously administered to the patient for 14 days. Following the use of the above pharmaceutical composition the level of haemoglobin was 163 g/l, the level of red blood cells was $5.24\times10^{12}$/l.

EXAMPLE 9. INTRAVENOUS ADMINISTRATION OF THE PHARMACEUTICAL COMPOSITION COMPRISING 4.0 WT % POLOXAMER TO A PERSON SUFFERING FROM THE MODERATE ANAEMIA

Volunteer patient V., woman, 66 years of age. Diagnosis: moderate anaemia. The initial level of haemoglobin was 82 g/l, the initial level of red blood cells was $2.83\times10^{12}$/l. Sterile pyrogen-free aqueous solution of the poloxamer comprising 4.0 wt % poloxamer-188 (Emuxol-268 of Grade "A"), 0.6 wt % sodium chloride, 0.039 wt % potassium chloride, 0.02 wt % magnesium chloride and water for injection as the remaining part. 30 ml of the poloxamer solution was intravenously administered to the patient for 14 days without using other standard treatment medications.

Following the use of the above pharmaceutical composition the level of haemoglobin was 105 g/l, the level of red blood cells was 3.91×10$^{12}$/l.

EXAMPLE 10. INTRAVENOUS ADMINISTRATION OF THE PHARMACEUTICAL COMPOSITION COMPRISING 13.3 WT % POLOXAMER TO A HEALTHY PERSON

Volunteer patient G., man, 53 years of age. Diagnosis: healthy. The initial level of haemoglobin was 151 g/l, the initial level of red blood cells was 4.75×10$^{12}$/l. Sterile pyrogen-free aqueous solution of the poloxamer comprising 13.3 wt % poloxamer-188 (Emuxol-268 of Grade "A"), 0.6 wt % sodium chloride and water for injection as the remaining part. 50 ml of the poloxamer solution was intravenously administered to the patient for 14 days. Following the use of the above pharmaceutical composition the level of haemoglobin was 161 g/l, the level of red blood cells was 5.32×10$^{12}$/l.

EXAMPLE 11. INTRAVENOUS ADMINISTRATION OF THE PHARMACEUTICAL COMPOSITION COMPRISING 16.0 WT % POLOXAMER TO A HEALTHY PERSON

Volunteer patient D., man, 49 years of age. Diagnosis: healthy. The initial level of haemoglobin was 153 WI, the initial level of red blood cells was 4.94×10$^{12}$/l. Sterile pyrogen-free aqueous solution of the poloxamer comprising 16.0 wt % poloxamer-188 (Emuxol-268 of Grade "A"), 0.6 wt % sodium chloride and water for injection as the remaining part. 50 ml of the poloxamer solution was intravenously administered to the patient for 14 days. Following the use of the above pharmaceutical composition the level of haemoglobin was 159 g/l, the level of red blood cells was 5.39×10$^{12}$/l.

EXAMPLE 12. ORAL ADMINISTRATION OF THE PHARMACEUTICAL COMPOSITION COMPRISING 13.3 WT % POLOXAMER TO A PERSON SUFFERING FROM THE CHRONIC IRON DEFICIENCY ANAEMIA

Volunteer patient H., woman, 32 years of age. Diagnosis: chronic iron deficiency anaemia. The initial level of haemoglobin was 110 g/l, the initial level of red blood cells was 3.6×10$^{12}$/l. Sterile pyrogen-free aqueous solution of the poloxamer comprising 13.3 wt % poloxamer-188 (Lutrol F68), 0.9 wt % sodium chloride and water for injection as the remaining part. The patient received orally 20 ml of the prepared poloxamer solution for 14 days without using other standard treatment medications. Following the use of the above pharmaceutical composition the level of haemoglobin was 130 g/I, the level of red blood cells was 4.31×10$^{12}$/l.

EXAMPLE 13. ORAL ADMINISTRATION OF THE PHARMACEUTICAL COMPOSITION COMPRISING 16.0 WT % POLOXAMER TO A HEALTHY PERSON

Volunteer patient Z., man, 25 years of age. Diagnosis: healthy. The initial level of haemoglobin was 155 g/l, the initial level of red blood cells was 5.16×10$^{12}$/l. Sterile pyrogen-free aqueous solution of the poloxamer comprising 16.0 wt % poloxamer-188 (Emuxol-268 of Grade "A"), 0.6 wt % sodium chloride and water for injection as the remaining part. The patient received orally 40 ml of the prepared poloxamer solution for 14 days. Following the use of the above pharmaceutical composition the level of haemoglobin was 161 g/l, the level of red blood cells was 5.31×10$^{12}$/l.

EXAMPLE 14. ORAL ADMINISTRATION OF THE PHARMACEUTICAL COMPOSITION COMPRISING 40.0 WT % POLOXAMER TO A PERSON SUFFERING FROM LYMPHOCYTIC LEUKAEMIA

Volunteer patient E., man, 65 years of age. Diagnosis: lymphocytic leukaemia. The initial level of haemoglobin was 90 g/l, the initial level of red blood cells was 2.97×10$^{12}$/l. Sterile pyrogen-free aqueous solution of the poloxamer comprising 40.0 wt % poloxamer-188 (Emuxol-268 of Grade "A"), 0.6 wt % sodium chloride and water for injection as the remaining part. The patient received orally 15 ml of the prepared poloxamer solution for 14 days without using other standard treatment medications. Following the use of the above pharmaceutical composition the level of haemoglobin was 94 g/l, the level of red blood cells was 3.00×10$^{12}$/l.

EXAMPLE 15. ORAL ADMINISTRATION OF THE PHARMACEUTICAL COMPOSITION COMPRISING 80.0 WT % POLOXAMER TO A PERSON SUFFERING FROM THE MILD ANAEMIA

Volunteer patient I., woman, 46 years of age. Diagnosis: mild anaemia. The initial level of haemoglobin was 93 g/l, the initial level of red blood cells was 3.18×10$^{12}$/l. The poloxamer-188 80.0 wt % (Lutrol F68) was dissolved in purified water to 100 ml. The patient received orally 30 ml for 14 days without using other standard treatment medications. Following the use of the above pharmaceutical composition the level of haemoglobin was 110 g/l, the level of red blood cells was 3.57×10$^{12}$/l.

EXAMPLE 16. ORAL ADMINISTRATION OF THE POLOXAMER TO A PERSON SUFFERING FROM THE MILD ANAEMIA

Volunteer patient A., woman, 43 years of age. Diagnosis: mild anaemia. The initial level of haemoglobin was 96 g/l, the initial level of red blood cells was 3.01×10$^{12}$/l. The patient received orally 1000 mg of the poloxamer-188 (Emuxol-268 of Grade "A") with a quarter cup of drinking water for 14 days without using other standard treatment medications. Following the use of the poloxamer-188 the level of haemoglobin was 109 g/l, the level of red blood cells was 3.59×10$^{12}$/l.

The study conducted revealed that levels of haemoglobin and red blood cells in the human blood after parenteral and oral administration of the poloxamer or pharmaceutical compositions thereof increased, furthermore, the inventors did not find any side effects.

The present invention is illustrated by the above examples, which are in no way intended to limit the subject matter of the present invention. The duration of treatment with the poloxamer, as well as a pharmaceutical composition comprising poloxamer, is 14 days, wherein each single dose may comprise poloxamer in the range of 10-2000 mg for rats, and in the range of 30-20000 mg for humans.

Thus, new pharmacologically active substances that promote a rise in haemoglobin and red blood cell levels in a patient's blood are identified, the use of which ensures the achievement of the technical result consisting in a significant reduction of the toxic effect and side effects of these substances on the patient's body in the case of oral and parenteral administration.

The invention claimed is:

1. A method for stimulating erythrocyte lineage in the bone marrow, which controls increasing the level of haemoglobin and red blood cells in a patient's blood, wherein
said level of haemoglobin and red blood cells in the patient's blood is determined and when said measures in the patient's blood are below normal or normal, said patient is administered daily during a course of treatment a pharmaceutical composition comprising at least 4% of poloxamer as a pharmacologically active substance, and the daily dosage of the composition is from 10 to 49 ml.

2. The method according to claim 1, wherein the pharmaceutical composition comprising an aqueous solution of the poloxamer is administered orally.

3. The method according to claim 1, wherein the pharmaceutical composition comprising a sterile aqueous solution of the poloxamer and at least one auxiliary substance is administered orally or intravenously.

4. The method according to claim 3, wherein sodium chloride is used as the auxiliary substance in the pharmaceutical composition comprising the sterile aqueous solution of the poloxamer.

5. The method according to claim 3 or claim 4, wherein the amount of the sterile aqueous solution of the poloxamer for oral and intravenous administrations is from 10 to 50 ml.

6. The method according to claim 3 or claim 4 wherein the concentration of the poloxamer in the aqueous solution for intravenous administration is from 4 to 16%.

7. The method according to claim 2, wherein the concentration of the poloxamer in the aqueous solution for oral administration is from 4 to 80%.

8. The method according to claim 1, wherein the pharmaceutical composition for oral administration is presented in the form of a tablet, an effervescent tablet, a capsule, a powder or an emulsion.

9. The method according to claim 4, wherein the content of the sodium chloride in the pharmaceutical composition is from 0.6% to 0.9%.

10. The method according to claim 2 or claim 3, wherein a course of treatment using the pharmaceutical composition is at least 14 days.

* * * * *